(12) United States Patent
Xu et al.

(10) Patent No.: US 9,765,022 B2
(45) Date of Patent: Sep. 19, 2017

(54) DISULFIDE COMPOUNDS FOR DELIVERY OF PHARMACEUTICAL AGENTS

(71) Applicant: Tufts University, Medford, MA (US)

(72) Inventors: Qiaobing Xu, Somerville, MA (US); Ming Wang, Somerville, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 14/770,327

(22) PCT Filed: Feb. 28, 2014

(86) PCT No.: PCT/US2014/019411
§ 371 (c)(1),
(2) Date: Aug. 25, 2015

(87) PCT Pub. No.: WO2014/134445
PCT Pub. Date: Sep. 4, 2014

(65) Prior Publication Data
US 2016/0009643 A1 Jan. 14, 2016

Related U.S. Application Data

(60) Provisional application No. 61/770,657, filed on Feb. 28, 2013.

(51) Int. Cl.
| | | |
|---|---|---|
| *C07C 323/12* | (2006.01) |
| *A61K 31/7088* | (2006.01) |
| *A61K 38/00* | (2006.01) |
| *C07B 45/06* | (2006.01) |
| *A61K 47/48* | (2006.01) |

(52) U.S. Cl.
CPC ........ *C07C 323/12* (2013.01); *A61K 31/7088* (2013.01); *A61K 38/00* (2013.01); *A61K 47/48046* (2013.01); *A61K 47/48869* (2013.01); *C07B 45/06* (2013.01)

(58) Field of Classification Search
None
See application file for complete search history.

(56) References Cited

U.S. PATENT DOCUMENTS

| | | | |
|---|---|---|---|
| 2002/0076443 A1* | 6/2002 | Stein .................... | A61K 9/0024 424/486 |
| 2011/0293703 A1 | 12/2011 | Mahon et al. | |
| 2012/0009222 A1 | 1/2012 | Nguyen et al. | |
| 2012/0277305 A1 | 11/2012 | Milne et al. | |

FOREIGN PATENT DOCUMENTS

| | | | | |
|---|---|---|---|---|
| JP | S55136261 | * | 10/1980 | ........... C07C 149/00 |
| WO | WO 98/13007 | * | 4/1998 | |
| WO | WO-03/106636 A2 | | 12/2003 | |
| WO | WO-2008/042973 A2 | | 4/2008 | |
| WO | WO 2013/012961 | * | 1/2013 | ............. A61K 47/48 |

OTHER PUBLICATIONS

JP S55-136261; Toyo Jozo Co., Ltd., Novel compunds for immunochemical analysis, 1980, English Translation, 27 pages.*
Akinc et al "A combinatorial Library of Lipid-Like Materials for Delivery of RNAi Therapeutics" Nature Biotechnology vol. 26, pp. 561-569, 2008.
Akinc et al "Development of Lipidoid-siRNA Formulations for Systemic Delivery to the Liver" Molecular Therapy vol. 17, pp. 872-879, 2009.
Nguyen et al "Lipid-Derived Nanoparticles for Immunostimulatory RNA Adjuvant Delivery" Proceedings of the National Academy of Sciences of the United States of America vol. 109, pp. E797-E803, 2012.
Place et al "Formulation of Small Activating RNA into Lipidoid Nanoparticles Inhibits Xenograft Prostate Tumor Growth by Inducing p21 Expression" Molecular Therapy—Nucleic Acids vol. 1, pp. 1-12, 2012.
Sun et al "Combinatorial Library of Lipidoids for In Vitro DNA Delivery" Bioconjugate Chemistry vol. 23, pp. 135-140, 2012.
Wang et al "A Combinatorial Library of Unsaturated Lipidoids for Efficient Intracellular Gene Delivery" American Chemical Society Synthetic Biology vol. 1, pp. 403-407, 2012.
Whitehead et al "Synergistic Silencing: Combinations of Lipid-Like Materials for Efficacious siRNA Delivery" Molecular Therapy vol. 19, pp. 1688-1694, 2011.
Ryu et al "Redox-Sensitive Disassembly of Amphiphilic Copolymer Based Micelles" Langmuir vol. 26, pp. 7086-7092, 2010.
Brodersen et al "Synthesis of Novel Amphiphilic Conjugates with a Biological Recognition Function for Developing Targeted Triggered Liposomal Delivery Systems" Tetrahedron vol. 67, pp. 7763-7774, 2011.
Fraix et al "Cationic Lipophosphoramidates with Two Disulfide Motifs: Synthesis, Behaviour in Reductive Media and Gene Transfection Activity" Organic & Biomolecular Chemistry vol. 11, pp. 1650-1658, 2013.
Goldenbogen et al "Reduction-Sensitive Liposomes from a Multifunctional Lipid Conjugate and Natural Phospholipids: Reduction and Release Kinetics and Cellular Uptake" Langmuir vol. 27, pp. 10820-10829, 2011.
Ohlsson et al "Analogues of Glycosphingolipids and Glycerolipids Suitable for Conjugation to Gold- and Amino-Functionalised Surfaces" Tetrahedron vol. 56, pp. 9975-9984, 2000.

(Continued)

*Primary Examiner* — Yate K Cutliff
(74) *Attorney, Agent, or Firm* — Cesari and McKenna, LLP

(57) ABSTRACT

A compound of formula the following formula: (I). In this formula, moieties A, B, X, $R_1$, $R_2$, and $R_3$ are defined herein. Also disclosed are a nanocomplex that is formed of such a compound and a pharmaceutical agent, and a nanocomplex that is formed of a protein and a bioreducible compound.

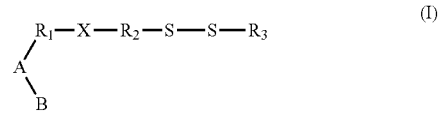

20 Claims, No Drawings

(56) References Cited

OTHER PUBLICATIONS

Samuel et al "Polymerized-Depolymerized Vesicles. Reversible Thiol-Disulfide-Based Phosphatidylcholine Membranes" Journal of the American Chemical Society vol. 107, pp. 42-47, 1985.

* cited by examiner

DISULFIDE COMPOUNDS FOR DELIVERY OF PHARMACEUTICAL AGENTS

CROSS REFERENCE TO RELATED APPLICATIONS

This application is the National Stage of International Application No. PCT/US2014/019411, filed on Feb. 28, 2014, which claims priority to U.S. Provisional Application No. 61/770,657, filed on Feb. 28, 2013, the contents of which are hereby incorporated by reference.

BACKGROUND

To achieve therapeutic effect, a drug must be delivered to its target site. It is a challenge to deliver a drug that is susceptible to enzymatic degradation or cannot cross cell membranes to reach an intracellular target.

Conventional delivery methods include use of target-specific vehicles. See Place et al., Molecular Therapy-Nucleic Acids, 1, e15 (2012). Examples of delivery vehicles include liposomes, polymers, and inorganic nanoparticles. See Gonzles-Toro et al., Journal of American Chemical Society, 134, 6964-67 (2012). However, these vehicles are often toxic or inefficient. See Sun et al., Bioconjugate Chemistry, 23, 135-40 (2012); and Akine et al., Molecular Therapy, 17, 872-79 (2009).

There is a need to develop an efficient and safe vehicle for delivering a drug to its target site.

SUMMARY

This invention is based on the discovery that certain lipid-like compounds are efficient and safe vehicles for use in delivery of pharmaceutical agents.

In one aspect, this invention features lipid-like compounds of formula (I):

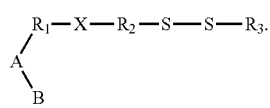

In this formula, A, a hydrophilic head and optionally positively charged, is

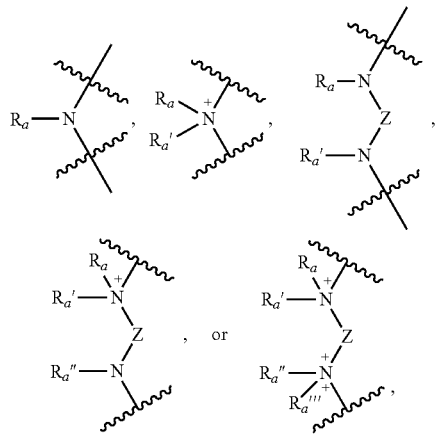

in which each of $R_a$, $R_a'$, $R_a''$, and $R_a'''$, independently, is H, a $C_1$-$C_{20}$ monovalent aliphatic radical, a $C_1$-$C_{20}$ monovalent heteroaliphatic radical, a monovalent aryl radical, or a monovalent heteroaryl radical, and Z is a $C_1$-$C_{20}$ bivalent aliphatic radical, a $C_1$-$C_{20}$ bivalent heteroaliphatic radical, a bivalent aryl radical, or a bivalent heteroaryl radical; B is a $C_1$-$C_{24}$ monovalent aliphatic radical, a $C_1$-$C_{24}$ monovalent heteroaliphatic radical, a monovalent aryl radical, a monovalent heteroaryl radical, or

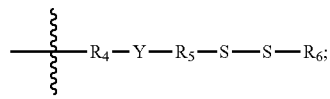

each of $R_1$ and $R_4$, independently, is a bond, a $C_1$-$C_{10}$ bivalent aliphatic radical, a $C_1$-$C_{10}$ bivalent heteroaliphatic radical, a bivalent aryl radical, or a bivalent heteroaryl radical; each of $R_2$ and $R_5$, independently, is a bond, a $C_1$-$C_{20}$ bivalent aliphatic radical, a $C_1$-$C_{20}$ bivalent heteroaliphatic radical, a bivalent aryl radical, or a bivalent heteroaryl radical; each of $R_3$ and $R_6$, independently, is a $C_1$-$C_{20}$ monovalent aliphatic radical, a $C_1$-$C_{20}$ monovalent heteroaliphatic radical, a monovalent aryl radical, or a monovalent heteroaryl radical; each of

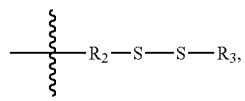

a hydrophobic tail, and

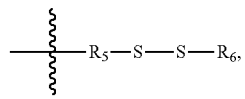

also a hydrophobic tail, has 8 to 24 carbon atoms; and each of X, a linker, and Y, also a linker, independently, is

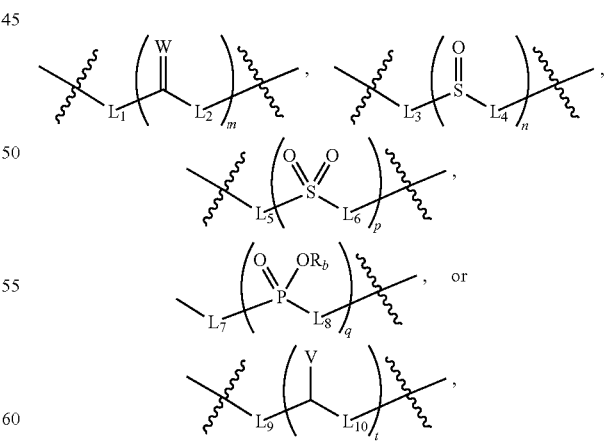

in which each of m, n, p, q, and t, independently, is 1-6; W is O, S, or $NR_c$; each of $L_1$, $L_3$, $L_5$, $L_7$, and $L_9$, directly linked to $R_1$, $R_2$, $R_4$, or $R_5$, independently, is a bond, O, S, or $NR_d$; each of $L_2$, $L_4$, $L_6$, $L_8$, and $L_{10}$, independently, is a bond, O, S, or $NR_e$; V is $OR_f$, $SR_g$, or $NR_hR_i$; and each of $R_b$, $R_c$, $R_d$, $R_e$, $R_f$, $R_g$, $R_h$, and $R_i$, independently, is H, OH, $C_{1-10}$ oxyaliphatic radical, $C_1$-$C_{10}$ monovalent aliphatic radical, $C_1$-$C_{10}$ monovalent heteroaliphatic radical, a monovalent aryl radical, or a monovalent heteroaryl radical.

A subset of the above-described lipid-like compounds include those in which A is

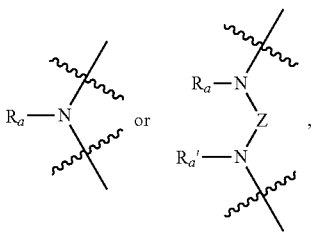

each of $R_a$ and $R_a'$, independently, being a $C_1$-$C_{10}$ monovalent aliphatic radical, a $C_1$-$C_{10}$ monovalent heteroaliphatic radical, a monovalent aryl radical, or a monovalent heteroaryl radical; and Z being a $C_1$-$C_{10}$ bivalent aliphatic radical, a $C_1$-$C_{10}$ bivalent heteroaliphatic radical, a bivalent aryl radical, or a bivalent heteroaryl radical.

Some lipid-like compounds of this invention feature each of $R_1$ and $R4$, independently, being $C_1$-$C_6$ (e.g., $C_1$-$C_4$) bivalent aliphatic radical or a $C_1$-$C_6$ (e.g., $C_1$-$C_4$) bivalent heteroaliphatic radical, the total carbon number for $R_2$ and $R_3$ being 12-20 (e.g., 14-18), the total carbon number of $R_5$ and $R_6$ also being 12-20 (e.g., 14-18), and each of X and Y, independently, is

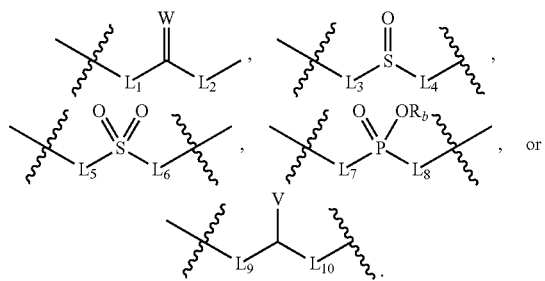

Specific examples of X and Y include

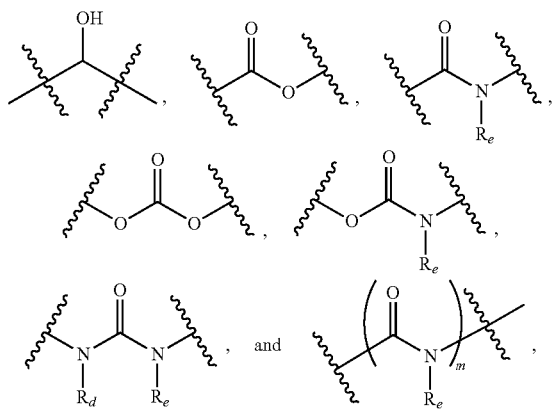

m being 2-6.

The term "aliphatic" herein refers to a saturated or unsaturated, linear or branched, acyclic, cyclic, or polycyclic hydrocarbon moiety. Examples include, but are not limited to, alkyl, alkylene, alkenyl, alkenylene, alkynyl, alkynylene, cycloalkyl, cycloalkylene, cycloalkenyl, cycloalkenylene, cycloalkynyl, and cycloalkynylene moieties. The term "alkyl" or "alkylene" refers to a saturated, linear or branched hydrocarbon moiety, such as methyl, methylene, ethyl, ethylene, propyl, propylene, butyl, butylenes, pentyl, pentylene, hexyl, hexylene, heptyl, heptylene, octyl, octylene, nonyl, nonylene, decyl, decylene, undecyl, undecylene, dodecyl, dodecylene, tridecyl, tridecylene, tetradecyl, tetradecylene, pentadecyl, pentadecylene, hexadecyl, hexadecylene, heptadecyl, heptadecylene, octadecyl, octadecylene, nonadecyl, nonadecylene, icosyl, icosylene, triacontyl, and triacotylene. The term "alkenyl" or "alkenylene" refers to a linear or branched hydrocarbon moiety that contains at least one double bond, such as —CH═CH—CH$_3$ and —CH═CH—CH$_2$—. The term "alkynyl" or "alkynylene" refers to a linear or branched hydrocarbon moiety that contains at least one triple bond, such as —C≡C—CH$_3$ and —C≡C—CH$_2$—. The term "cycloalkyl" or "cycloalkylene" refers to a saturated, cyclic hydrocarbon moiety, such as cyclohexyl and cyclohexylene. The term "cycloalkenyl" or "cycloalkenylene" refers to a non-aromatic, cyclic hydrocarbon moiety that contains at least one double bond, such as cyclohexenyl cyclohexenylene. The term "cycloalkynyl" or "cycloalkynylene" refers to a non-aromatic, cyclic hydrocarbon moiety that contains at least one triple bond, cyclooctynyl and cyclooctynylene.

The term "heteroaliphatic" herein refers to an aliphatic moiety containing at least one heteroatom selected from N, O, P, B, S, Si, Sb, Al, Sn, As, Se, and Ge.

The term "oxyaliphatic" herein refers to an —O-aliphatic. Examples of oxyaliphatic include methoxy, ethoxy, n-propoxy, isopropoxy, n-butoxy, iso-butoxy, sec-butoxy, and tert-butoxy.

The term "aryl" herein refers to a $C_6$ monocyclic, $C_{10}$ bicyclic, $C_{14}$ tricyclic, $C_{20}$ tetracyclic, or $C_{24}$ pentacyclic aromatic ring system. Examples of aryl groups include phenyl, phenylene, naphthyl, naphthylene, anthracenyl, anthrcenylene, pyrenyl, and pyrenylene. The term "heteroaryl" herein refers to an aromatic 5-8 membered monocyclic, 8-12 membered bicyclic, 11-14 membered tricyclic, and 15-20 membered tetracyclic ring system having one or more heteroatoms (such as O, N, S, or Se). Examples of heteroaryl groups include furyl, furylene, fluorenyl, fluorenylene, pyrrolyl, pyrrolylene, thienyl, thienylene, oxazolyl, oxazolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolyl, isoquinolylene, indolyl, and indolylene.

Unless specified otherwise, aliphatic, heteroaliphatic, oxyaliphatic, alkyl, alkylene, alkenyl, alkenylene, alkynyl, alkynylene, cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl mentioned herein include both substituted and unsubstituted moieties. Possible substituents on cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on aliphatic, heteroaliphatic, oxyaliphatic, alkyl, alkylene, alkenyl, alkenylene, alkynyl, and alkynylene include all of the above-recited substituents except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl can also be fused with each other.

The lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Another aspect of this invention relates to a pharmaceutical composition containing a pharmaceutically acceptable carrier and a nanocomplex formed of one of the lipid compounds described above and a pharmaceutical agent. In this composition, the nanocomplex has a particle size of 50 to 500 nm (e.g., 50 to 300 nm and 50 to 180 nm); the pharmaceutical agent is a small molecule, a protein, a peptide, a nucleic acid, a saccharide, or a combination thereof; and the compound binds to the pharmaceutical agent via a non-covalent interaction, a covalent bond, or both.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active glycoside compound. Examples of other carriers include colloidal silicon oxide, magnesium stearate, cellulose, sodium lauryl sulfate, and D&C Yellow #10.

The term "pharmaceutical agent" refers to any chemical substance intended for use in the medical diagnosis, cure, treatment, or prevention of disease.

The term "small molecule" refers to an organic compound having a molecular weight less than 800 Dalton (e.g., less than 500 Dalton), including oligopeptides, oligosaccharides, and oligonucleotides.

The term "peptide" or "protein" refers to a polymer of natural or non-natural amino acids linked together by amide bonds and having a molecular weight of 800 Dalton or higher. The term "nucleic acid" refers to a polymer of nucleotides linked together by phosphodiester bonds, having a molecular weight of 800 Dalton or higher. Both of these polymers can be chemically modified. Examples of protein modification include PEGylation and carboxylation of amine groups in lysine residues contained therein. More specifically, carboxylation of proteins or peptides can be achieved by using cis-aconitic anhydride. See Lee et al., Angewandte Chemie International Edition, 48, 5309-12 (2009); Lee et al., Angewandte Chemie International Edition, 49, 2552-55 (2010); and Maier et al., Journal of the American Chemical Society, 134, 10169-73 (2012).

The term "non-covalent interaction" refers to any non-covalent binding, which includes ionic interaction, hydrogen bonding, van der Waals interaction, and hydrophobic interaction.

Still within the scope of this invention is a pharmaceutical composition containing a nanocomplex that is formed of a protein and a bioreducible compound. In this pharmaceutical composition, the nanocomplex has a particle size of 50 to 500 nm; the bioreducible compound contains a disulfide hydrophobic moiety, a hydrophilic moiety, and a linker joining the disulfide hydrophobic moiety and the hydrophilic moiety; and the protein binds to the bioreducible compound via a non-covalent interaction, a covalent bond, or both.

In certain embodiments, the disulfide hydrophobic moiety is a heteroaliphatic radical containing one or more —S—S— groups and 8 to 24 carbon atoms; the hydrophilic moiety is an aliphatic or heteroaliphatic radical containing one or more hydrophilic groups and 1-20 carbon atoms, each of the hydrophilic groups being amino, alkylamino, dialkylamino, trialkylamino, tetraalkylammonium, hydroxyamino, hydroxyl, carboxyl, carboxylate, carbamate, carbamide, carbonate, phosphate, phosphite, sulfate, sulfite, or thiosulfate; and the linker is O, S, Si, $C_1$-$C_6$ alkylene,

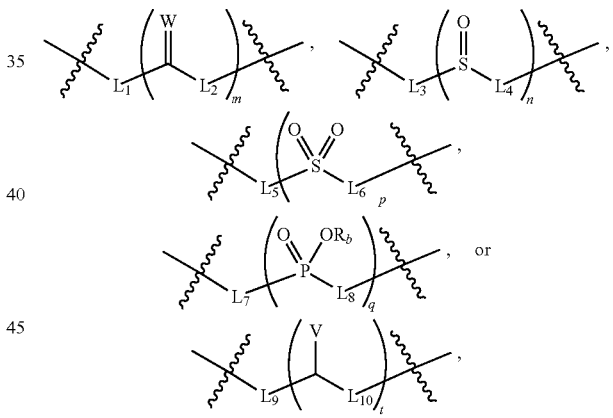

in which each of the variables is defined above.

Specific examples of X and Y include O, S, Si, $C_1$-$C_6$ alkylene,

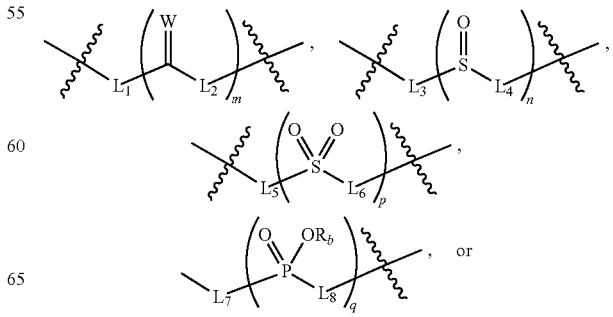

-continued

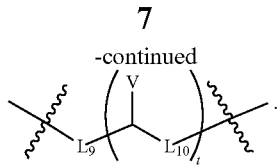
5

The details of one or more embodiments of the invention are set forth in the description below. Other features, objects, and advantages of the invention will be apparent from the description and from the claims.

DETAILED DESCRIPTION

The lipid-like compounds of this invention, as shown in formula (I) above, each include (i) a hydrophilic head, A; (ii) a hydrophobic tail, $R_2$—S—S—$R_3$; and (iii) a linker, X. Optionally, these compounds contain a second hydrophobic tail, $R_5$—S—S—$R_6$ and a second linker, Y.

The hydrophilic head contains one or more hydrophilic functional groups, e.g., hydroxyl, carbonyl, carboxyl, amino, sulfhydryl, phosphate, amide, ester, ether, carbamate, carbonate, carbamide, and phosphodiester. These groups can form hydrogen bonds and are optionally positively or negatively charged.

Examples of the hydrophilic head include:

1
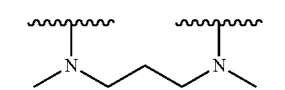

2
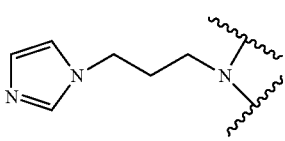

3
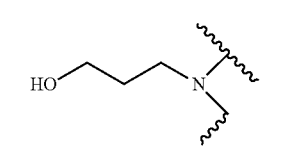

4
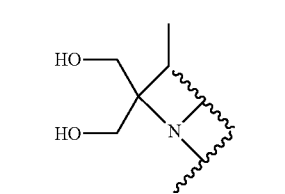

5
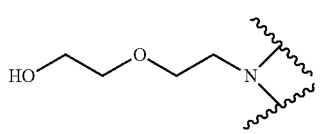

6
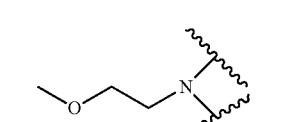

7
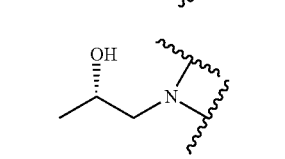

-continued

8
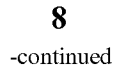

9
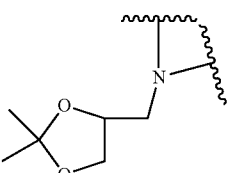

10
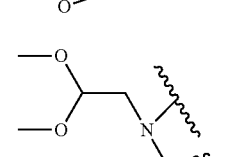

11
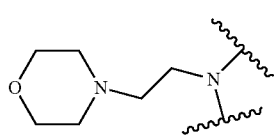

12
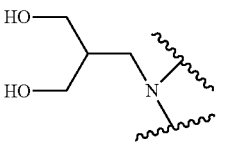

13
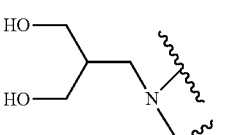

14
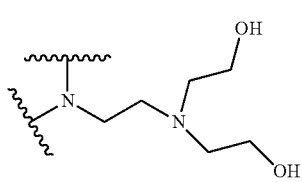

15
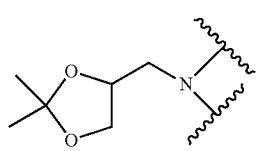

16
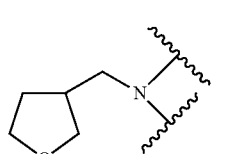

17
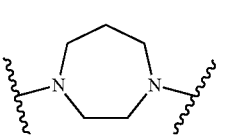

-continued

18
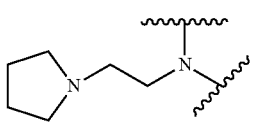

19
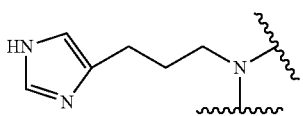

20
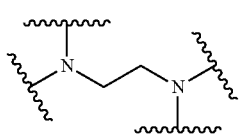

21
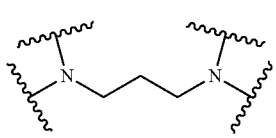

22
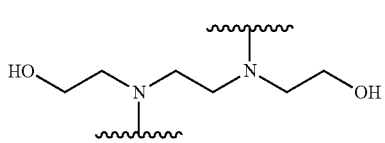

23
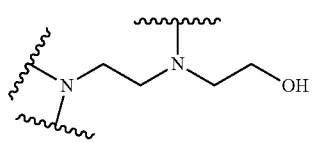

24
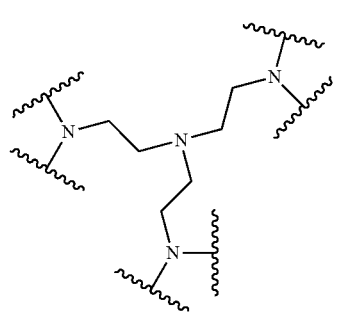

25
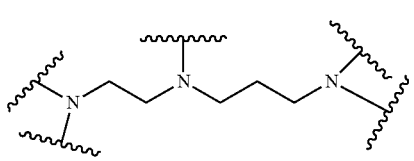

26

-continued

27
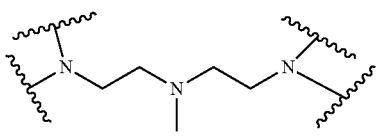

28
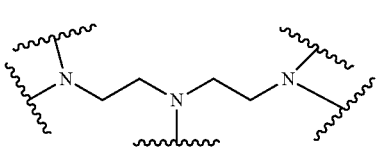

29
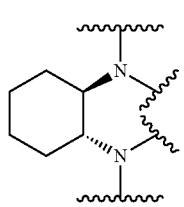

30
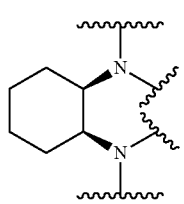

31
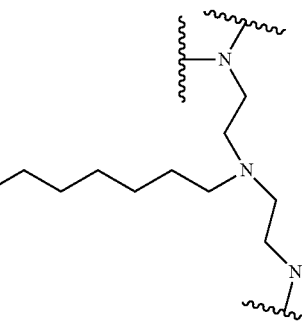

32
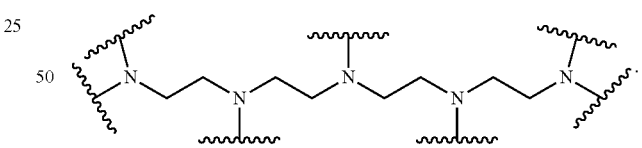

Other examples include those described in Akine et al., Nature Biotechnology, 26, 561-69 (2008) and Mahon et al., US Patent Application Publication 2011/0293703.

The hydrophobic tail is a saturated or unsaturated, linear or branched, acyclic or cyclic, aromatic or nonaromatic hydrocarbon moiety containing a disulfide bond and 8-24 carbon atoms. One or more of the carbon atoms can be replaced with a heteroatom, such as N, O, P, B, S, Si, Sb, Al, Sn, As, Se, and Ge. The tail is optionally substituted with one or more groups described in the Summary section. The lipid-like compounds containing this disulfide bond can be bioreducible.

Examples include:

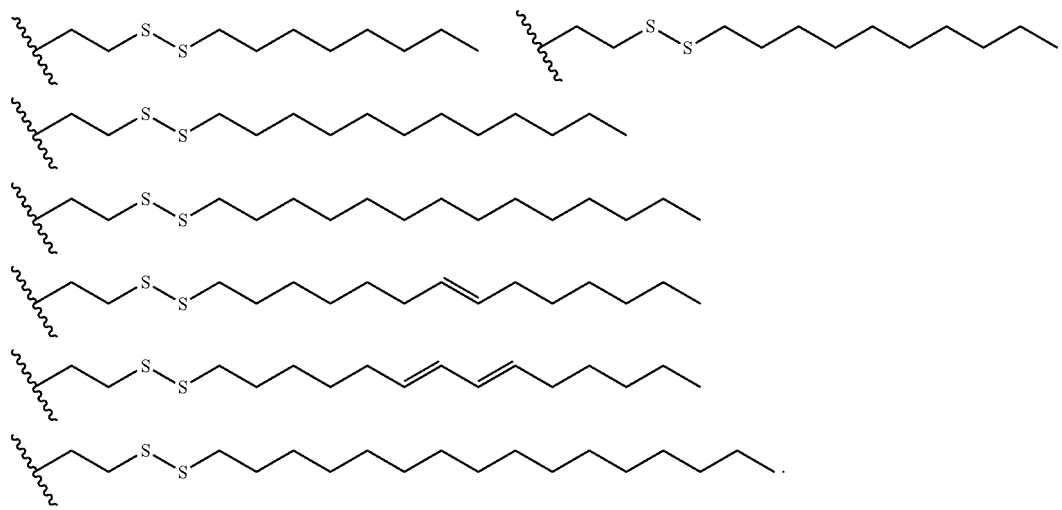

Turning to the linker(s), it links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate, phosphate, phosphite, sulfate, sulfite, and thiosulfate. Examples include:

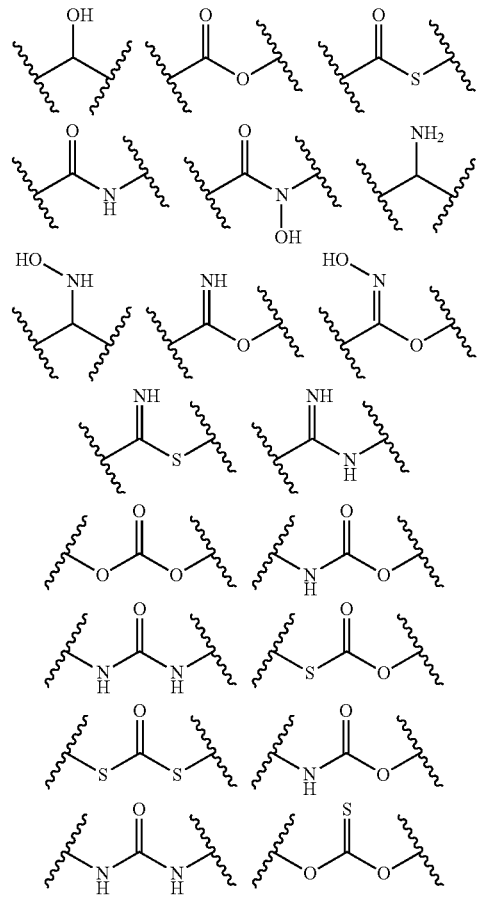

-continued

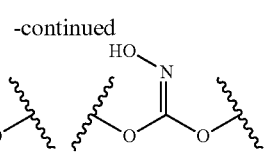

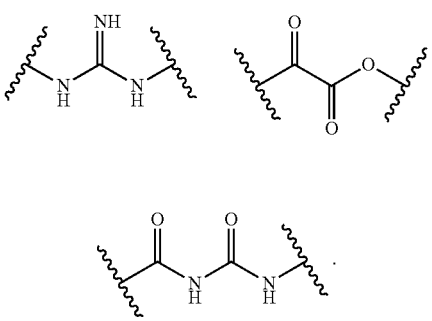

Shown below are exemplary lipid-like compounds of this invention:

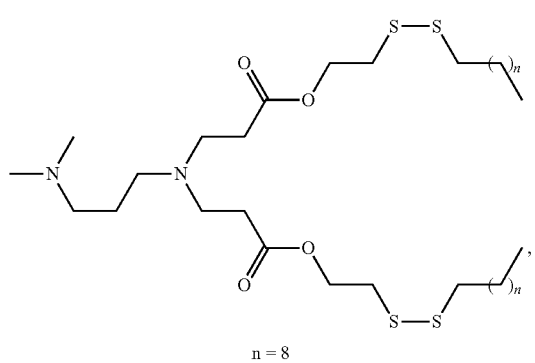

80-O14B n = 8

80-O16B
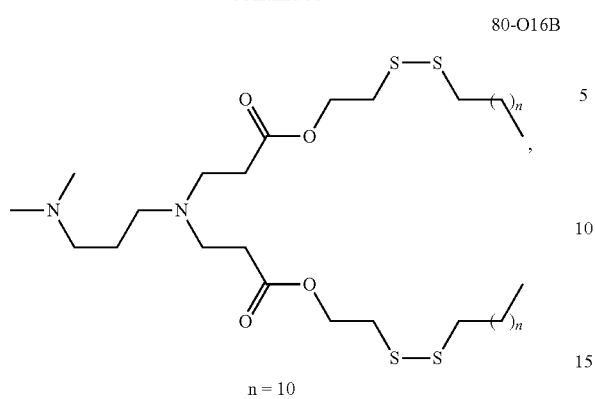
n = 10
80-O18B
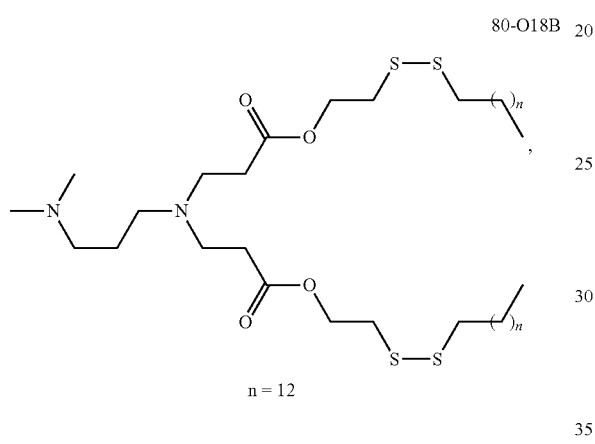
n = 12
87-O14B
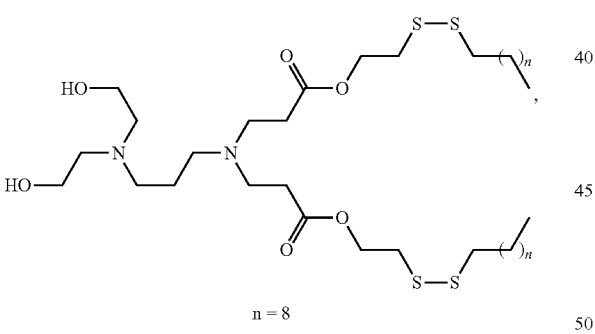
n = 8
87-O16B
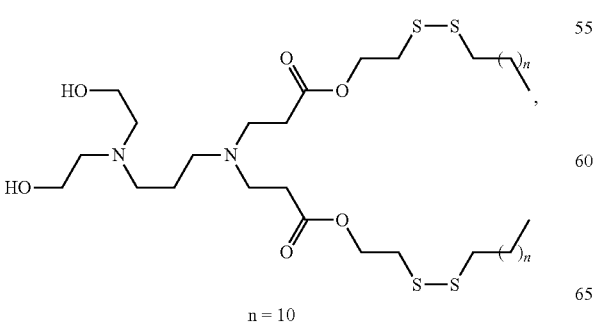
n = 10
87-O18B
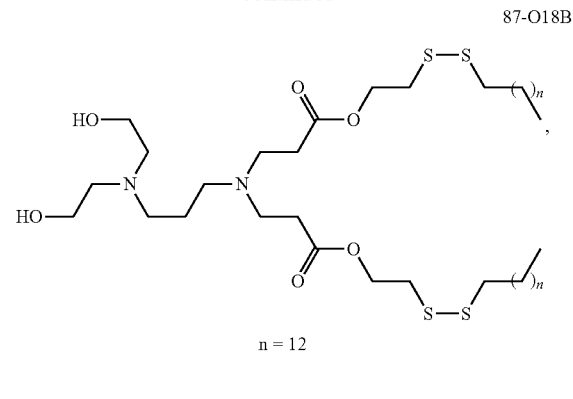
n = 12
1-O16B
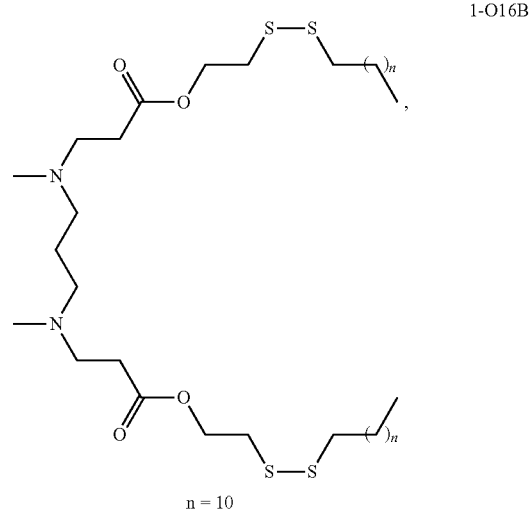
n = 10
1-O18B
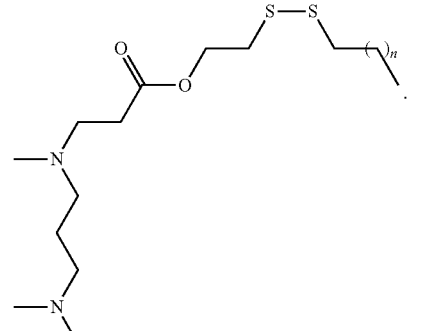
n = 12
The lipid-like compounds of this invention can be prepared by methods well known in the art. See Wang et al., ACS Synthetic Biology, 1, 403-07 (2012); Manoharan, et al., International Patent Application Publication WO 2008/042973; and Zugates et al., U.S. Pat. No. 8,071,082.
The route shown below exemplifies synthesis of these lipid-like compounds:

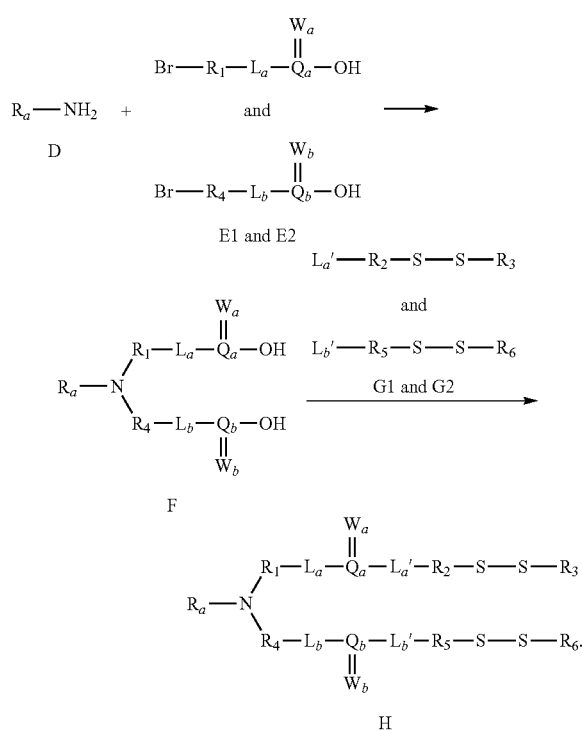

Each of $L_a$, $L_a'$, $L_b$, and $L_b'$ can be one of $L_1$-$L_{10}$; each of $W_a$ and $W_b$, independently, is W or V; and $R_a$ and $R_1$-$R_6$ are defined above, as well as $L_1$-$L_{10}$, W, and V.

In this exemplary synthetic route, an amine compound, i.e., compound D, reacts with bromides E1 and E2 to form compound F, which is then coupled with both G1 and G2 to afford the final product, i.e., compound H. One or both of the double bonds in this compound (shown above) can be reduced to one or two single bonds to obtain different lipid-like compounds of this invention.

Other lipid-like compounds of this invention can be prepared using other suitable starting materials through the above-described synthetic route and others known in the art. The method set forth above can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis ($2^1$ ed., John Wiley and Sons 2009) and subsequent editions thereof.

Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

As mentioned above, these lipid-like compounds are useful for delivery of pharmaceutical agents. They can be preliminarily screened for their efficacy in delivering pharmaceutical agents by an in vitro assay and then confirmed by animal experiments and clinic trials. Other methods will also be apparent to those of ordinary skill in the art.

Not to be bound by any theory, the lipid-like compounds facilitate delivery of pharmaceutical agents by forming complexes, e.g., nanocomplexes and microparticles. The hydrophilic head of such a lipid-like compound, positively or negatively charged, binds to a moiety of a pharmaceutical agent that is oppositely charged and its hydrophobic moiety binds to a hydrophobic moiety of the pharmaceutical agent. Either binding can be covalent or non-covalent.

The above described complexes can be prepared using procedures described in publications such as Wang et al., ACS Synthetic Biology, 1, 403-07 (2012). Generally, they are obtained by incubating a lipid-like compound and a pharmaceutical agent in a buffer such as a sodium acetate buffer or a phosphate buffered saline ("PBS").

Further, this invention covers a method of administering an effective amount of the complexes (e.g., nanocomplexes) described above to a patient in need. "An effective amount" refers to the amount of complexes that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having the above-described complexes can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having the complexes can also be administered in the form of suppositories for rectal administration.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of Lipid-Like Compounds

Eight lipid-like compounds were prepared following the procedure described below.

In a 5-mL Telfon-lined glass screw-top vial, acrylate with disulfide bonds was added to amine at a molar ratio of 1:2.4 (amine:acrylate). The mixture was stirred at 90° C. for two days. After cooling, the lipid-like compound thus formed was used without purification unless otherwise noted. Optionally, it was purified using a flash chromatography on silica gel and characterized by proton nuclear magnetic resonance.

Following the above-described procedure, compound 80-O14B was prepared using N,N'-dimehtylpropane-1,3-diamine and 2-(decyldisulfanyl)ethyl acrylate, which have the structures shown below:

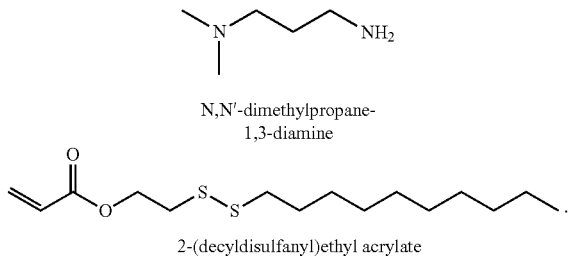

N,N'-dimethylpropane-1,3-diamine 2-(decyldisulfanyl)ethyl acrylate

EXAMPLE 2

Synthesis of Lipid-Like Compound 80-O16B

Compound 80-O16B was prepared following exactly the same procedure described in Example 1 except that 2-(dodecyldisulfanyl)ethyl acrylate (structure shown below) was used instead of 2-(decyldisulfanyl)ethyl acrylate.

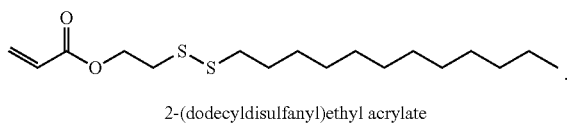 [SMILES: C=CC(=O)OCCSSCCCCCCCCCCCC]

2-(dodecyldisulfanyl)ethyl acrylate

EXAMPLE 3

Synthesis of Lipid-Like Compound 80-O18B

Compound 80-O18B was prepared following exactly the same procedure described in Example 1 except that 2-(tetradecyldisulfanyl)ethyl acrylate (structure shown below) was used instead of 2-(decyldisulfanyl)ethyl acrylate.

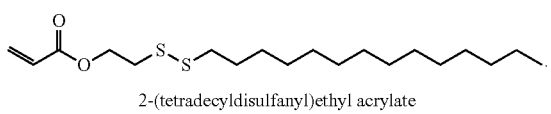 [SMILES: C=CC(=O)OCCSSCCCCCCCCCCCCCC]

2-(tetradecyldisulfanyl)ethyl acrylate

EXAMPLE 4

Synthesis of Lipid-Like Compound 87-O14B

Compound 87-O14B was prepared following exactly the same procedure described in Example 1 except that 2,2'-(3-aminopropylazanediyl)diethanol (structure shown below) was used instead of N,N'-dimehtylpropane-1,3-diamine.

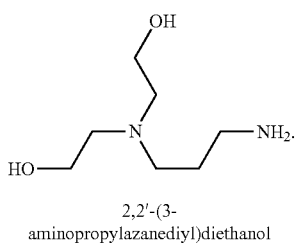 [SMILES: NCCCN(CCO)CCO]

2,2'-(3-aminopropylazanediyl)diethanol

EXAMPLE 5

Synthesis of Lipid-Like Compound 87-O16B

Compound 87-O16B was prepared following exactly the same procedure described in Example 2 except that 2,2'-(3-aminopropylazanediyl)diethanol was used instead of N,N'-dimehtylpropane-1,3-diamine.

EXAMPLE 6

Synthesis of Lipid-Like Compound 87-O18B

Compound 87-O18B was prepared following exactly the same procedure described in Example 3 except that 2,2'-(3-aminopropylazanediyl)diethanol was used instead of N,N'-dimehtylpropane-1,3-diamine.

EXAMPLE 7

Synthesis of Lipid-Like Compound 1-O16B

Compound 1-O16B was prepared following exactly the same procedure described in Example 2 except that $N^1,N^3$-dimethylpropane-1,3-diamine (structure shown below) was used instead of N,N'-dimehtylpropane-1,3-diamine.

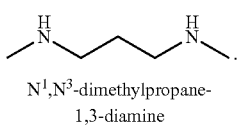

N¹,N³-dimethylpropane-
1,3-diamine

EXAMPLE 8

Synthesis of Lipid-Like Compound 1-O18B

Compound 1-O18B was prepared following exactly the same procedure described in Example 7 except that 2-(tetradecyldisulfanyl)ethyl acrylate was used instead of 2-(dodecyldisulfanyl)ethyl acrylate.

EXAMPLES 9-45

Preparation of Nanocomplex Compositions

The lipid-like compound prepared in one of Examples 1-8 was dissolved in sodium acetate solution (25 mM, pH=5.5) at a concentration of 1 mg/mL. Optionally, cholesterol and 1,2-dioleoyl-sn-glycero-3-phosphoethanolamine ("DOPE") were also included. A protein or siRNA was introduced to the resulting mixture, which was incubated for 15 minutes at room temperature. The weight ratio between the lipid-like compound solution and the protein or siRNA is 6:1, 20:1, or 40:1. The nanocomplex compositions thus prepared, i.e., Compositions 9-30 described below, were subjected to an in vitro assay described in Example 47 below.

Compositions 9-30 were prepared following the above-described procedure using disulfide lipid-like compounds 80-O14B, 80-O16B, 80-O18B, 87-O14B, 87-O16B, and 87-O18B of this invention, all of which are bioreducible. See the table below for the components and their amounts (in μg) of these compositions and others, each containing a lipid-like compound, cholesterol, DOPE, and a protein (e.g., saporin) or siRNA. Note that in this table, the components and their weights for Compositions 31-45 of this invention and comparative compositions described below are also included. Comparative Composition 9'-30' were prepared in the same manner except that non-bioreducible lipid-like compounds 80-O14, 80-O16, 80-O18, 87-O14, 87-O16, and 87-O18 were used. Preparation of these non-bioreducible compounds is described below.

| | Composition by weight |
|---|---|
| Composition 9 | 80-O14B (16 μg), cholesterol (8 μg), DOPE (1 μg), and saporin (0.8 μg) |
| Comparative 9' | 80-O14 (16 μg), cholesterol (8 μg), DOPE (1 μg), and saporin (0.8 μg) |
| Composition 10 | 80-O16B (16 μg), cholesterol (8 μg), DOPE (1 μg), and saporin (0.8 μg) |
| Comparative 10' | 80-O16 (16 μg), cholesterol (8 μg), DOPE (1 μg), and saporin (0.8 μg) |
| Composition 11 | 80-O18B (16 μg), cholesterol (8 μg), DOPE (1 μg), and saporin (0.8 μg) |
| Comparative 11' | 80-O18 (16 μg), cholesterol (8 μg), DOPE (1 μg), and saporin (0.8 μg) |
| Composition 12 | 87-O16B (16 μg), cholesterol (8 μg), DOPE (1 μg), and saporin (0.8 μg) |
| Comparative 12' | 87-O16 (16 μg), cholesterol (8 μg), DOPE (1 μg), and saporin (0.8 μg) |
| Composition 13 | 80-O14B (16 μg), cholesterol (8 μg), DOPE (1 μg), and saporin (0.4 μg) |
| Comparative 13' | 80-O14 (16 μg), cholesterol (8 μg), DOPE (1 μg), and saporin (0.4 μg) |
| Composition 14 | 80-O16B (16 μg), cholesterol (8 μg), DOPE (1 μg), and saporin (0.4 μg) |
| Comparative 14' | 80-O16 (16 μg), cholesterol (8 μg), DOPE (1 μg), and saporin (0.4 μg) |
| Composition 15 | 80-O18B (16 μg), cholesterol (8 μg), DOPE (1 μg), and saporin (0.4 μg) |
| Comparative 15' | 80-O18 (16 μg), cholesterol (8 μg), DOPE (1 μg), and saporin (0.4 μg) |
| Composition 16 | 87-O16B (16 μg), cholesterol (8 μg), DOPE (1 μg), and saporin (0.4 μg) |
| Comparative 16' | 87-O16 (16 μg), cholesterol (8 μg), DOPE (1 μg), and saporin (0.4 μg) |
| Composition 17 | 80-O14B (8 μg), cholesterol (4 μg), DOPE (1 μg), and saporin (0.4 μg) |
| Comparative 17' | 80-O14 (8 μg), cholesterol (4 μg), DOPE (1 μg), and saporin (0.4 μg) |
| Composition 18 | 80-O16B (8 μg), cholesterol (4 μg), DOPE (1 μg), and saporin (0.4 μg) |
| Comparative 18' | 80-O16 (8 μg), cholesterol (4 μg), DOPE (1 μg), and saporin (0.4 μg) |
| Composition 19 | 80-O18B (8 μg), cholesterol (4 μg), DOPE (1 μg), and saporin (0.4 μg) |
| Comparative 19' | 80-O18 (8 μg), cholesterol (4 μg), DOPE (1 μg), and saporin (0.4 μg) |
| Composition 20 | 87-O16B (8 μg), cholesterol (4 μg), DOPE (1 μg), and saporin (0.4 μg) |
| Comparative 20' | 87-O16 (8 μg), cholesterol (4 μg), DOPE (1 μg), and saporin (0.4 μg) |
| Composition 21 | 80-O14B (8 μg), cholesterol (4 μg), DOPE (1 μg), and saporin (0.2 μg) |
| Comparative 21' | 80-O14 (8 μg), cholesterol (4 μg), DOPE (1 μg), and saporin (0.2 μg) |
| Composition 22 | 80-O16B (8 μg), cholesterol (4 μg), DOPE (1 μg), and saporin (0.2 μg) |
| Comparative 22' | 80-O16 (8 μg), cholesterol (4 μg), DOPE (1 μg), and saporin (0.2 μg) |
| Composition 23 | 80-O18B (8 μg), cholesterol (4 μg), DOPE (1 μg), and saporin (0.2 μg) |
| Comparative 23' | 80-O18 (8 μg), cholesterol (4 μg), DOPE (1 μg), and saporin (0.2 μg) |
| Composition 24 | 87-O16B (8 μg), cholesterol (4 μg), DOPE (1 μg), and saporin (0.2 μg) |
| Comparative 24' | 87-O16 (8 μg), cholesterol (4 μg), DOPE (1 μg), and saporin (0.2 μg) |
| Composition 25 | 80-O14B (7.2 μg) and siRNA (1.2 μg) |
| Comparative 25' | 80-O14 (7.2 μg) and siRNA (1.2 μg) |
| Composition 26 | 87-O14B (7.2 μg) and siRNA (1.2 μg) |
| Comparative 26' | 87-O14 (7.2 μg) and siRNA (1.2 μg) |
| Composition 27 | 80-O16B (7.2 μg) and siRNA (1.2 μg) |
| Comparative 27' | 80-O16 (7.2 μg) and siRNA (1.2 μg) |
| Composition 28 | 87-O16B (7.2 μg) and siRNA (1.2 μg) |
| Comparative 28' | 87-O16 (7.2 μg) and siRNA (1.2 μg) |
| Composition 29 | 80-O18B (7.2 μg) and siRNA (1.2 μg) |
| Comparative 29' | 80-O18 (7.2 μg) and siRNA (1.2 μg) |
| Composition 30 | 87-O18B (7.2 μg) and siRNA (1.2 μg) |
| Comparative 30' | 87-O18 (7.2 μg) and siRNA (1.2 μg) |
| Composition 31 | 1-O16B (16 μg), cholesterol (4 μg), DOPE (1 μg), and saporin (1.07 μg) |
| Composition 32 | 1-O18B (16 μg), cholesterol (4 μg), DOPE (1 μg), and saporin (1.07 μg) |
| Comparative 33a' | 80-O14 (16 μg), cholesterol (4 μg), and DOPE (1 μg) |
| Comparative 33b' | 80-O14 (16 μg), cholesterol (4 μg), DOPE (1 μg), and saporin (2 μg) |
| Comparative 33c' | 80-O14B (16 μg), cholesterol (4 μg), and DOPE (1 μg) |
| Composition 33 | 80-O14B (16 μg), cholesterol (4 μg), DOPE (1 μg), and saporin (2 μg) |
| Comparative 34a' | 80-O16 (16 μg), cholesterol (4 μg), and DOPE (1 μg) |
| Comparative 34b'' | 80-O16 (16 μg), cholesterol (4 μg), DOPE (1 μg), and saporin (2 μg) |
| Comparative 34c' | 80-O16B (16 μg), cholesterol (4 μg), and DOPE (1 μg) |
| Composition 34 | 80-O16B (16 μg), cholesterol (4 μg), DOPE (1 μg), and saporin (2 μg) |
| Comparative 35a' | 80-O18 (16 μg), cholesterol (4 μg), and DOPE (1 μg) |

| Composition by weight | |
|---|---|
| Comparative 35b' | 80-O18 (16 µg), cholesterol (4 µg), DOPE (1 µg), and saporin (2 µg) |
| Comparative 35c' | 80-O18B (16 µg), cholesterol (4 µg), and DOPE (1 µg) |
| Composition 35 | 80-O18B (16 µg), cholesterol (4 µg), DOPE (1 µg), and saporin (2 µg) |
| Comparative 36' | 80-O14B (16 µg), cholesterol (4 µg), DOPE (1 µg), and 0% PEG |
| Composition 36 | 80-O14B (16 µg), cholesterol (4 µg), DOPE (1 µg), saporin (2 µg), and 0% PEG |
| Comparative 37' | 80-O14B (16 µg), cholesterol (4 µg), DOPE (1 µg), and 25% PEG |
| Composition 37 | 80-O14B (16 µg), cholesterol (4 µg), DOPE (1 µg), saporin (2 µg), and 25% PEG |
| Comparative 38' | 80-O14B (16 µg), cholesterol (4 µg), DOPE (1 µg), and 40% PEG |
| Composition 38 | 80-O14B (16 µg), cholesterol (4 µg), DOPE (1 µg), saporin (2 µg), and 40% PEG |
| Comparative 39' | 80-O14B (16 µg) and cholesterol (4 µg) |
| Composition 39 | 80-O14B (16 µg), cholesterol (4 µg), and saporin (2 µg) |
| Comparative 40' | 80-O14B (16 µg) and DOPE (1 µg) |
| Composition 40 | 80-O14B (16 µg), DOPE (1 µg), and saporin (2 µg) |
| Comparative 41' | 80-O14B (16 µg) |
| Composition 41 | 80-O14B (16 µg) and saporin (2 µg) |
| Composition 42 | 80-O16B (16 µg), cholesterol (4 µg), DOPE (1 µg), PEG (1 µg), and siRNA (2 µg) |
| Composition 43 | 80-O16B (16 µg), cholesterol (4 µg), DOPE (1 µg), PEG (4 µg), and siRNA (2 µg) |
| Composition 44 | 87-O18B (16 µg), cholesterol (4 µg), DOPE (1 µg), PEG (1 µg), and siRNA (2 µg) |
| Composition 45 | 80-O16B (16 µg), PEG (4 µg), and siRNA (2 µg) |

Compositions 31 and 32 were prepared using a thin film hydration method described below. Compound 1-O16B or 1-O18B, cholesterol, and DOPE were mixed at a weight ratio of 16:4:1 in chloroform, which was then evaporated under vacuum, leaving a thin film. Re-hydrating the thin film in PBS yielded a solution of 1-O16B or 1-O18B at a concentration of 1 mg/mL. Saporin was added (1-O16B or 1-O18B solution:saporin=15:1 by weight). The mixture was incubated for 15 minutes at room temperature followed by addition of mPEG2000-ceramide C16/DSPE-PEG2000-Biotin (purchased from Avanti Polar Lipids, weight/weight=8:1, PEG 10% by weight of 1-O16B, this component not shown in the table above). The mixture was again incubated for 15 minutes to yield a nanocomplex composition, Composition 31 or 32. See the table above for the weight ratios between Compound 1-O16B or 1-O18B, cholesterol, DOPE, and saporin. These two compositions thus prepared were subjected to an in vivo assay described in Example 47 below.

Compositions 33-35 were prepared following the procedure described immediately above except that mPEG2000-ceramide (not shown in the table above), instead of mPEG2000-ceramide C16/DSPE-PEG2000-Biotin, and lipid-like compounds 80-O14B, 80-O16B, and 80-O18B were used, respectively. Similarly, Comparative Compositions 33a'-33c', 34a'-34c', and 35a'-35c' were prepared using 80-O14, 80-O16, or 80-O18 without the addition of saporin. These compositions were tested in the in vitro assay described in Example 47.

Composition 36 was prepared following the procedure used to prepare Composition 33, except that no DSPE-PEG2000 was included. Comparative Composition 36' was also prepared in a similar manner without the addition of any saporin. These two compositions, as well as nine Compositions 37-45 and five Comparative Compositions 37'-41' described below, were subjected to an in vitro and in vivo assay described in Example 47.

Composition 37 was prepared following the procedure used to prepare Composition 33, except that DSPE-PEG2000 was added in an amount such that PEG was 25% by weight of the lipid-like compound. Comparative Composition 37' was also prepared in a similar manner without the addition of any saporin.

Composition 38 was prepared following the procedure used to prepare Composition 33, except that DSPE-PEG2000 was added at the amount that PEG was 40% by weight of the lipid-like compound. Comparative Composition 38' was prepared in a similar manner without the addition of any saporin.

Composition 39 was prepared following the procedure described below. Compound 80-14B and cholesterol were mixed at a weight ratio of 16:4 in chloroform, which was then evaporated under vacuum, leaving a thin film. Re-hydrating the thin film in PBS yielded a solution of 80-14B at a concentration of 1 mg/mL. Saporin was added (80-O14B:saporin=8:1 by weight). The mixture was incubated for 15 minutes at room temperature followed by addition of DSPE-PEG2000 (PEG 10% by weight of 80-O14B). The mixture was again incubated for 15 minutes to yield Composition 39. Comparative Composition 39' was also prepared in a similar manner without the addition of any saporin.

Composition 40 was prepared following the procedure used to prepare Composition 39 described above, except that DOPE (80-14B:DOPE=16:1, w/w), instead of cholesterol, was added. Comparative Composition 40' was also prepared in a similar manner without the addition of any saporin.

Composition 41 was prepared following the procedure used to prepare Composition 39 described above, except that no cholesterol was added. Comparative Composition 41' was also prepared in a similar manner without the addition of any saporin.

Composition 42 was prepared following the procedure described below. Compound 80-16B, cholesterol, and DOPE were mixed at a weight ratio of 16:4:1 in chloroform, which was then evaporated under vacuum, leaving a thin film. Re-hydrating the thin film in PBS yielded a solution of 80-O16B at a concentration of 1 mg/mL. siRNA was added (80-O16B:siRNA=8:1 by weight). The mixture was incubated for 15 minutes at room temperature followed by addition of DSPE-PEG2000 (80-O16B:PEG=16:1, w/w). The mixture was again incubated for 15 minutes to yield Composition 42.

Composition 43 was prepared following the procedure described immediately above, except that the ratio between 80-16B and PEG was 4:1, instead of 16:1.

Composition 44 was prepared following the procedure used to prepared Composition 42, except that 87-18B, instead of 80-16B, was used.

Composition 45 was prepared following the procedure used to prepare Composition 43, except that no cholesterol and DSPE-PEG2000 were included.

Preparation of Comparative Compounds and Comparative Compositions

Comparative compounds 80-O14, 80-O16, 80-O18, 87-O14, 87-O16, and 87-O18 were prepared using exactly the same method described in Examples 1-6, respectively, except that tetradecyl acrylate, hexadecyl acrylate, or octadecyl acrylate was used instead of a disulfanyl acrylate. The structures of these six comparative compounds are shown below:

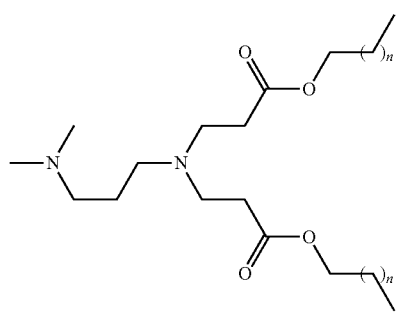

Comparative compound 80-O14, n = 12
Comparative compound 80-O16, n = 14
Comparative compound 80-O18, n = 16

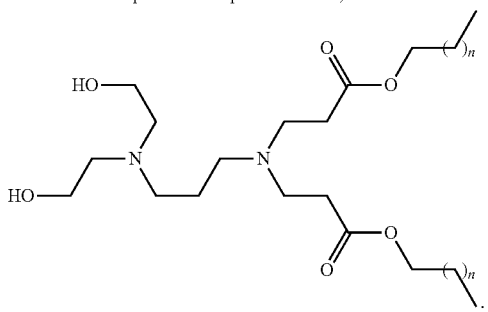

Comparative compound 87-O14, n = 12
Comparative compound 87-O16, n = 14
Comparative compound 87-O18, n = 16

Using these six comparative compounds, comparative compositions 9'-30' 33a'-33c', 34a'-34c', 35a'-35c', and 36'-41' were prepared following exactly one of the procedures described above and tested following the procedures described in Example 47 below. The above table shows the components and their amounts contained in these compositions.

EXAMPLE 46

Particle Size Measurement

A dynamic light scattering (DLS) assay was conducted to determine the particle size for nanocomplexes contained in each of Compositions 33 and 36-41 and also Comparative Composition 33b' and 36'-41'.

Approximately 20 µL of a 1 mg/mL nanocomplex composition was diluted to 1.2 mL phosphate buffer (pH=7.2) for this measurement.

In each of the 16 tested compositions, the particle size was between 150 to 400 nm. Note that the particle size could be tuned by changing components and their amounts contained in a composition.

EXAMPLE 47

Evaluation of Lipid-Like Compounds' Delivery Efficiency

The lipid-like compounds prepared in Examples 1-6 were evaluated for delivering a protein, i.e., saporin (from Saponaria officinalis, pI=9.5), into cell lines MDA-MB-231 and MCF-7, and delivering an siRNA, i.e., siPLK-1, into cell line GFP-MDA-MB-231.

Cell Culture

Three cells lines were cultured in Dulbecco's Modified Eagle Medium ("DMEM") supplemented with 10% Fetal Bovine Serum ("FBS") and 1% penicillin/streptomycin at 37° C. in the presence of 5% $CO_2$. For the protein transfection assay described below, cells were seeded in 96-well plates at a density of 10,000 cells per well a day prior to transfection.

In Vitro Protein Transfection in MDA-MB-231

To evaluate protein delivery efficiency, lipid-like compound/protein complexes prepared in Examples 9-24 and comparative compositions 9'-24' were added to MDA-MB-231 cancer cells and incubated at 37° C. for 24 hours. The saporin concentration was 0.1 µg/250 µL in PBS. The same volume of PBS without any lipid-like compound or saporin was used as a control. The cell viability was determined by the Alamar Blue assay after 24 hours of incubation. All transfection studies were performed in quadruplicate.

Unexpectedly, disulfide lipid-like compounds 80-O14B, 80-O16B, 80-O18B, and 87-O16B demonstrated much greater saporin delivery efficiency under all four studied conditions than their non-disulfide counterparts, i.e., 80-O14, 80-O16, 80-O18, and 87-O16. More specifically, cells treated with Compositions 13 (containing 80-O14B), 14 (containing 80-O16B), 15 (containing 80-O18B), and 16 (containing 87-O16B) showed, respectively, cell viabilities of 32%, 9%, 12%, and 39%. By contrast, cells treated with Comparative Compositions 13' (containing 80-O14), 14' (containing 80-O16), 15' (containing 80-O18), and 16' (containing 87-O16) showed, respectively, cell viabilities of 80%, 57%, 51%, and 72%.

In Vitro Protein Transfection in MCF-7

Compositions 33-41, as well as Comparative Compositions 33a', 33b', 33c', 34a', 34b', 34c', 35a', 35b', 35c', and 36'-41', were subjected to an in vitro study for delivery of saporin into MCF-7 cells. More Specifically, each of the formulations were diluted in PBS to varying concentrations from 0.025 to 3 µg/50 µL, which was subsequently delivered to the cells prepared in the 96-well plate at four trials per formulation. Various concentrations of saporin were tested. PBS was run as blank.

Cell viability was determined by an MTT assay. The MTT reagent 3-(4,5-dimethylthiazol-2-yl)-2,5-diphenyltetrazolium bromide was diluted to 0.5 mg/mL in DMEM to obtain an assay solution. The media was aspirated from the 96-well plate used for delivery experiments. Each well was then filled with 150 µL of the MTT assay solution and incubated at 37° C. for 4 hours. Absorbance was read at 590 nm. Saporin was labeled with FITC (fluorescein isothiocyanate) as follows. Saporin (1 mg/mL; 200 µL) was combined with 6 mg FITC dissolved in 100 µL DMSO, and, protected from light, subsequently spun for seven hours. The protein thus labeled was separated from FITC dye via a size exclusion column A FITC-labeled saporin fraction was obtained and diluted to a concentration of 0.67 mg/mL for absorbance measurement. $IC_{50}$ values were calculated as the concentration of a lipid compound at which cell viability decreased to 50%.

Unexpectedly, Compositions 33 (containing 80-O14B), 34 (containing 80-O-16B), and 35 (containing 80-O-18B) showed $IC_{50}$ values of 0.75 µg/10000 cells, 0.6 µg/10000 cells, and 0.8 µg/10000 cells, respectively. By contrast, Comparative Compositions 33b' (containing 80-O14), 34b' (containing 80-O-16), and 35b' (containing 80-O-18) showed no cytotoxicity at the concentration of 1 µg/10000 cells.

In Vitro siRNA Delivery

To evaluate siRNA delivery efficiency, lipid-like compound/siRNA complexes prepared in Examples 25-30 and comparative compositions 25'-30' were added to GFP-MDA-MB-231 cancer cells and incubated at 37° C. for 24 hours. A control composition was used, which contained the complex of siRNA and Lipofectamine 2000 ("LPF 2000;" a commercial cationic lipid purchased from Invitrogen) in OPTI-MEM prepared following the manufacturer's instructions. The percentage of GFP expressing cells was evaluated by a flow cytometer (BD FACS caliber). All compositions were tested in quadruplicate.

Unexpectedly, compositions containing one of disulfide lipid-like compounds 80-O16B, 80-O18B, 87-O14B, and 87-O16B each inhibited GFP expression to 40% or lower. By contrast, their non-disulfide counterparts 80-O16, 80-O18, 87-O14, and 87-O16 each inhibited GFP expression to 75% or higher.

In Vivo Cancer Treatment

Composition 31 (i.e., containing 1-O16B and saporin) and Composition 32 (i.e., containing 1-O18B and saporin) were tested for in vivo inhibiting tumor growth following the procedure described below. More specifically, BALB/c mice bearing 4T1-12B breast tumors were developed from a 4T1-12B cell suspension in DMEM supplemented with 10% FBS at a concentration of $10^7$ cells/mL. An aliquot (100 μL) of the cell suspension was injected into the mammary fat pad of 4-6 week-old female BALB/c mice. The mice were sorted into four groups randomly (n=7 for treatment group, n=5 for control groups) seven days after the injection. The mice were injected through tail-vein every three days. For the treatment group, each mouse was injected with 5.5 mg/kg of 1-O16B or 1-O18B and 330 μg/kg of saporin. Tumor volumes were measured every three days.

PBS without 1-O16B, 1-O18B, and saporin was also injected as a control. Comparative studies were also conducted using saporin in PBS without 1-O16B and 1-O18B.

Unexpectedly, at Day 16, mice treated with Composition 31 or 32 had a tumor size of less than 100 mm$^3$, much smaller than that for mice treated with PBS (i.e., 200 mm$^3$) and those treated with saporin (i.e., more than 120 mm$^3$); and at Day 22, mice treated with Composition 32 had a tumor size of 100 mm$^3$, much smaller than that in mice treated with PBS or saporin (i.e., more than 250 mm$^3$).

In Vivo siRNA Delivery

To evaluate in vivo siRNA delivery efficiency, Compositions 42-45 were used to carry out the delivery assay described below. These compositions were formulated using siRNA that targets glyceraldehyde 3-phosphate dehydrogenase (GAPDH), following the procedure described above.

Test animal mice were divided into four groups (5 mice/group), receiving Composition 42, 43, 44, or 45 via intravenous tail vein injection. Mice in the control group received PBS. Organ-specific suppression efficiency and accumulation were examined in the liver, lung, and kidney tissues.

Unexpectedly, Compositions 42 and 43 suppressed gene expression in the lung tissue, Composition 44 in the liver tissue, and Composition 45 in the kidney tissue. More specifically, in the lung tissue of mice treated with Compositions 42 and 43, GAPDH mRNA were expressed at 37% and 56% of the level in the control group; in the liver tissue of mice treated with Composition 44, 55% of GAPDH mRNA was expressed; and in the kidney tissue of mice treated with Composition 45, 25% of GAPDH mRNA was expressed.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

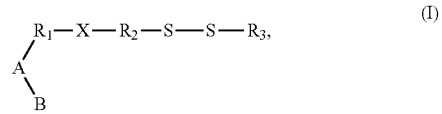

wherein

A, a hydrophilic head, is

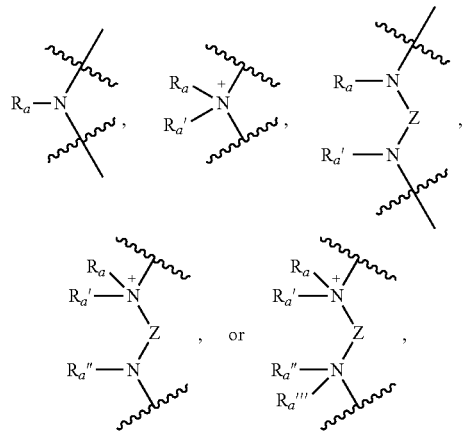

in which each of $R_a$, $R_a'$, $R_a''$, and $R_a'''$, independently, is H, a $C_1$-$C_{20}$ monovalent aliphatic radical, a $C_1$-$C_{20}$ monovalent heteroaliphatic radical, a monovalent aryl radical, or a monovalent heteroaryl radical; and Z is a $C_1$-$C_{20}$ bivalent aliphatic radical, a $C_1$-$C_{20}$ bivalent heteroaliphatic radical, a bivalent aryl radical, or a bivalent heteroaryl radical;

B is a $C_1$-$C_{24}$ monovalent aliphatic radical, a $C_1$-$C_{24}$ monovalent heteroaliphatic radical, a monovalent aryl radical, a monovalent heteroaryl radical, or

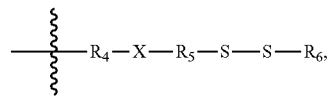

in which $R_4$, $R_5$, $R_6$, and Y are defined below;
each of $R_1$ and $R_4$, independently, is a $C_1$-$C_{10}$ bivalent aliphatic radical, a $C_1$-$C_{10}$ bivalent heteroaliphatic radical, a bivalent aryl radical, or a bivalent heteroaryl radical;
each of $R_2$ and $R_5$, independently, is a bond, a $C_1$-$C_{20}$ bivalent aliphatic radical, a $C_1$-$C_{20}$ bivalent heteroaliphatic radical, a bivalent aryl radical, or a bivalent heteroaryl radical;

each of $R_3$ and $R_6$, independently, is a $C_1$-$C_{20}$ monovalent aliphatic radical; a $C_1$-$C_{20}$ monovalent heteroaliphatic radical, a monovalent aryl radical, or a monovalent heteroaryl radical;
each of

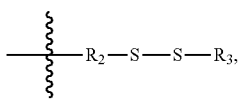

a hydrophobic tail, and

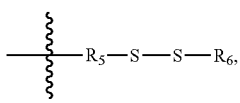

also a hydrophobic tail, has 8 to 24 carbon atoms; and each of X, a linker, and Y, also a linker, independently, is

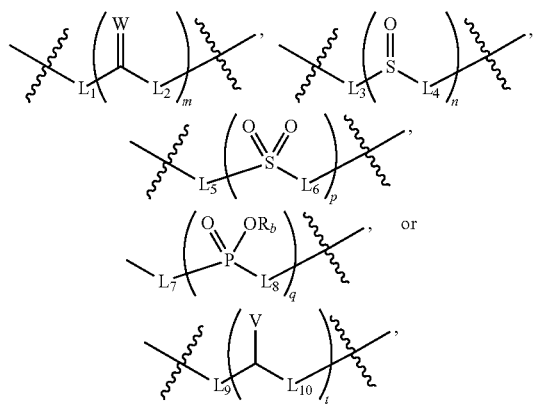

in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of $L_2$, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, $C_1$-$C_{10}$ oxyaliphatic radical, $C_1$-$C_{10}$ monovalent aliphatic radical, $C_1$-$C_{10}$ monovalent heteroaliphatic radical, a monovalent aryl radical, or a monovalent heteroaryl radical.

2. The compound of claim 1, wherein A is

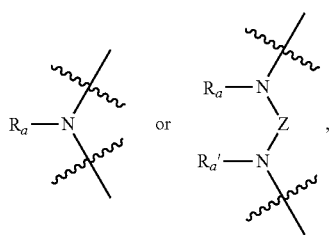

in which each of $R_a$ and $R_a'$, independently, is, H, a $C_1$-$C_{10}$ monovalent aliphatic radical, a $C_1$-$C_{10}$ monovalent heteroaliphatic radical, a monovalent aryl radical, or a monovalent heteroaryl radical; and Z is a $C_1$-$C_{10}$ bivalent aliphatic radical, a $C_1$-$C_{10}$ bivalent heteroaliphatic radical, a bivalent aryl radical, or a bivalent heteroaryl radical.

3. The compound of claim 2, wherein B is a $C_8$-$C_{20}$ monovalent aliphatic radical, a $C_8$-$C_{20}$ monovalent heteroaliphatic radical, a monovalent aryl radical, or a monovalent heteroaryl radical; $R_1$ is a $C_1$-$C_6$ bivalent aliphatic radical, or a $C_1$-$C_6$ bivalent heteroaliphatic radical; the total carbon number of $R_2$ and $R_3$ is 12-20; and X is

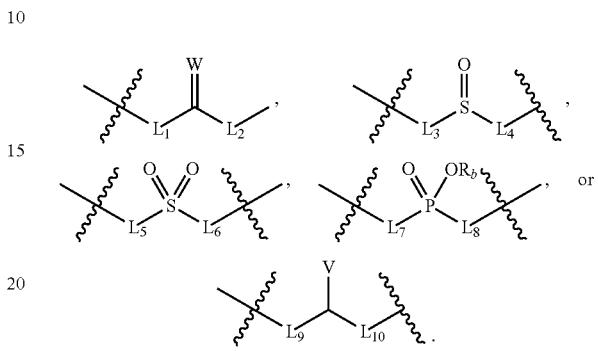

4. The compound of claim 2, wherein B is

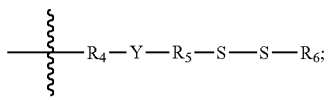

each of $R_1$ and $R_4$ is a $C_1$-$C_6$ bivalent aliphatic radical or a $C_1$-$C_6$ bivalent heteroaliphatic radical; the total carbon number of $R_2$ and $R_3$ is 12-20; the total carbon number of $R_5$ and $R_6$ is 12-20; and each of X and Y, independently, is

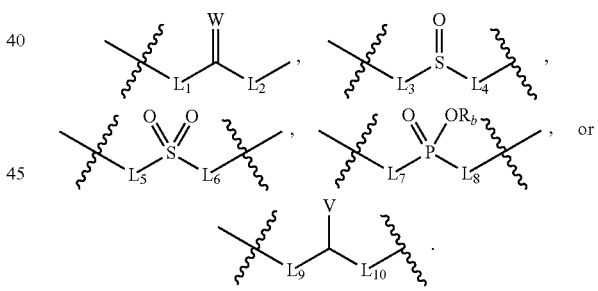

5. The compound of claim 1, wherein B is a $C_8$-$C_{20}$ monovalent aliphatic radical, a $C_8$-$C_{20}$ monovalent heteroaliphatic radical, a monovalent aryl radical, or a monovalent heteroaryl radical; $R_1$ is a $C_1$-$C_6$ bivalent aliphatic radical or a $C_1$-$C_6$ bivalent heteroaliphatic radical; the total carbon number of $R_2$ and $R_3$ is 12-20; and X is

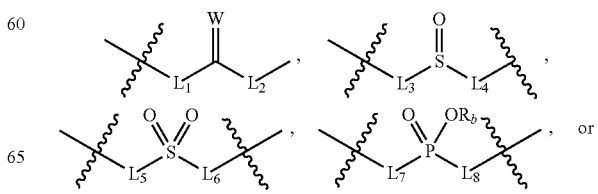

-continued

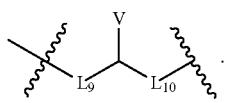

6. The compound of claim 1, wherein B is

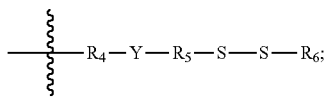

each of $R_1$ and $R_4$ is a $C_1$-$C_6$ bivalent aliphatic radical or a $C_1$-$C_6$ bivalent heteroaliphatic radical; the total carbon number of $R_2$ and $R_3$ is 12-20; the total carbon number of $R_5$ and $R_6$ is 12-20; and each of X and Y, independently, is

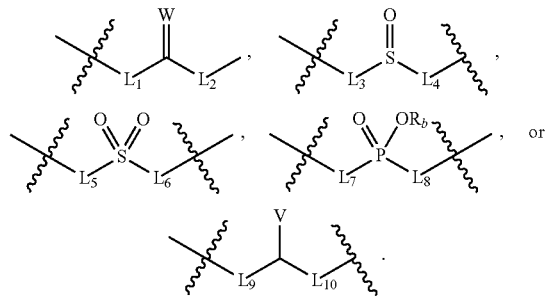

7. The compound of claim 1, wherein $R_1$ is a $C_1$-$C_4$ bivalent aliphatic radical or a $C_1$-$C_4$ bivalent heteroaliphatic radical; and the total carbon number of $R_2$ and $R_3$ is 14-18.

8. The compound of claim 1, wherein X is

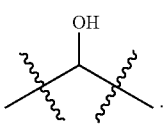 [SMILES: *C(*)O]

9. The compound of claim 1, wherein X is

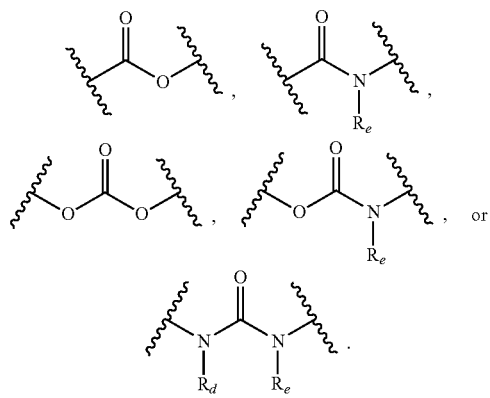

10. The compound of claim 1, wherein X is

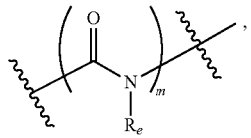

in which m is 2-6.

11. A pharmaceutical composition comprising a pharmaceutically acceptable carrier and a nanocomplex formed of a compound of claim 1 and a pharmaceutical agent, wherein the nanocomplex has a particle size of 50 nm to 1000 nm; the compound binds to the pharmaceutical agent via a non-covalent interaction, a covalent bond, or both; and the pharmaceutical agent is a small molecule, a protein, a peptide, a nucleic acid, or a combination thereof.

12. The pharmaceutical composition of claim 11, wherein A is

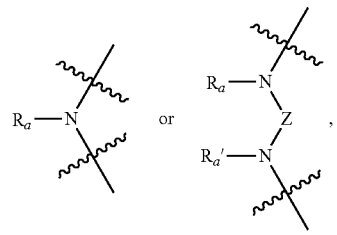

in which each of $R_a$ and $R_a'$, independently, is a $C_1$-$C_{10}$ monovalent aliphatic radical, a $C_1$-$C_{10}$ monovalent heteroaliphatic radical, a monovalent aryl radical, or a monovalent heteroaryl radical; and Z is a $C_1$-$C_{10}$ bivalent aliphatic radical, a $C_1$-$C_{10}$ bivalent heteroaliphatic radical, a bivalent aryl radical, or a bivalent heteroaryl radical.

13. The pharmaceutical composition of claim 12, wherein B is a $C_8$-$C_{20}$ monovalent aliphatic radical, a $C_8$-$C_{20}$ monovalent heteroaliphatic radical, a monovalent aryl radical, or a monovalent heteroaryl radical; $R_1$ is a $C_1$-$C_6$ bivalent aliphatic radical or a $C_1$-$C_6$ bivalent heteroaliphatic radical; the total carbon number of $R_2$ and $R_3$ is 12-20; and X is

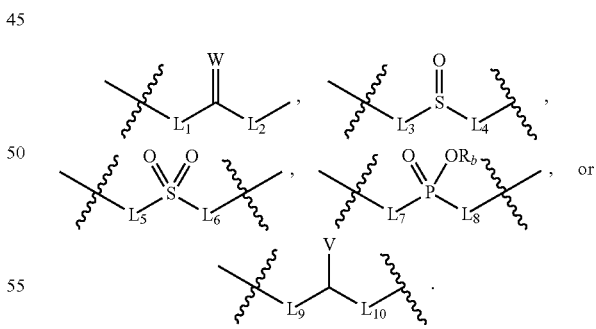

14. The pharmaceutical composition of claim 12, wherein B is

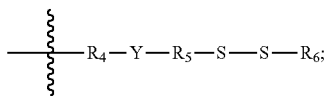

each of $R_1$ and $R_4$ is a $C_1$-$C_6$ bivalent aliphatic radical or a $C_1$-$C_6$ bivalent heteroaliphatic radical; the total carbon number of $R_2$ and $R_3$ is 12-20; the total carbon number of $R_5$ and $R_6$ is 12-20; and each of X and Y, independently, is

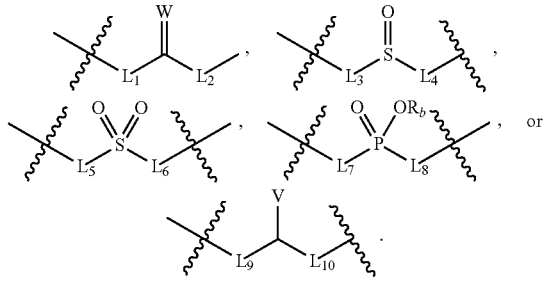

15. The pharmaceutical composition of claim 11, wherein B is a $C_8$-$C_{20}$ monovalent aliphatic radical, a $C_8$-$C_{20}$ monovalent heteroaliphatic radical, a monovalent aryl radical, or a monovalent heteroaryl radical; $R_1$ is a $C_1$-$C_6$ bivalent aliphatic radical or a $C_1$-$C_6$ bivalent heteroaliphatic radical; the total carbon number of $R_2$ and $R_3$ is 12-20; and X is

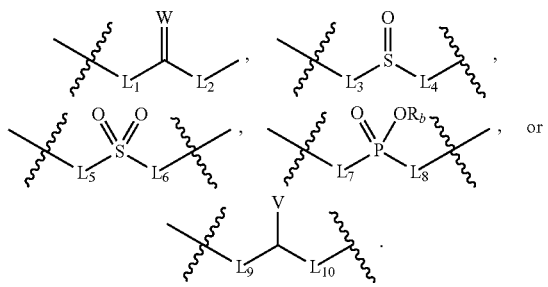

16. The pharmaceutical composition of claim 11, wherein B is

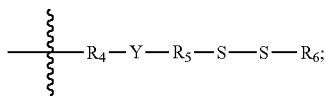

each of $R_1$ and $R_4$ is a $C_1$-$C_6$ bivalent aliphatic radical or a $C_1$-$C_6$ bivalent heteroaliphatic radical; the total carbon number of $R_2$ and $R_3$ is 12-20; the total carbon number of $R_5$ and $R_6$ is 12-20; and each of X and Y, independently, is

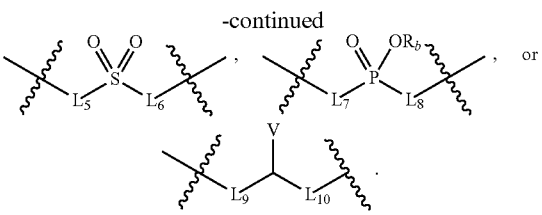

17. The pharmaceutical composition of claim 11, wherein $R_1$ is a $C_1$-$C_4$ bivalent aliphatic radical or a $C_1$-$C_4$ bivalent heteroaliphatic radical; the total carbon number of $R_2$ and $R_3$ is 14-18.

18. The pharmaceutical composition of claim 11, wherein X is

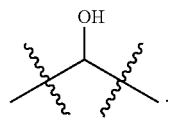

19. The pharmaceutical composition of claim 11, wherein X is

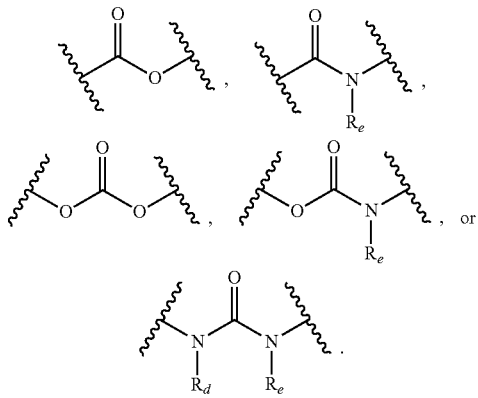

20. The pharmaceutical composition of claim 11, wherein X is

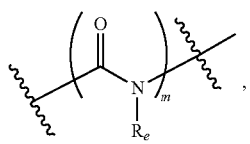

in which m is 2-6.

* * * * *